(12) United States Patent
Kang et al.

(10) Patent No.: US 9,517,045 B2
(45) Date of Patent: Dec. 13, 2016

(54) RADIOGRAPHIC IMAGING APPARATUS AND A METHOD OF CORRECTING THRESHOLD ENERGIES IN A PHOTON-COUNTING RADIOGRAPHIC DETECTOR

(71) Applicant: SAMSUNG ELECTRONICS CO., LTD., Suwon-si (KR)

(72) Inventors: Ji Hoon Kang, Hwaseong-si (KR); Sang Min Lee, Suwon-si (KR); Min Kook Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 105 days.

(21) Appl. No.: 14/483,574

(22) Filed: Sep. 11, 2014

(65) Prior Publication Data

US 2015/0146849 A1    May 28, 2015

(30) Foreign Application Priority Data

Nov. 25, 2013    (KR) ........................ 10-2013-0143788

(51) Int. Cl.
   *A61B 6/00*    (2006.01)
   *A61B 6/03*    (2006.01)
   *G01T 7/00*    (2006.01)
   *G01N 23/087*    (2006.01)

(52) U.S. Cl.
   CPC ............. *A61B 6/585* (2013.01); *A61B 6/4233* (2013.01); *A61B 6/4241* (2013.01); *A61B 6/58* (2013.01);

(Continued)

(58) Field of Classification Search
   CPC ..... A61B 6/032; A61B 6/4208; A61B 6/4233; A61B 6/4241; A61B 6/58; A61B 6/582; A61B 6/585

(Continued)

(56) References Cited

U.S. PATENT DOCUMENTS 4,284,895 A * 8/1981 Morgan ................. A61B 6/032
                                                 250/363.02
5,461,232 A * 10/1995 McCandless .......... A61B 6/037
                                                 250/363.04

(Continued)

FOREIGN PATENT DOCUMENTS

JP        2011-516852 A        5/2011

OTHER PUBLICATIONS

Communication dated May 20, 2015 issued by the Korean Intellectual Property Office in counterpart Application No. 10-2013-0143788.

*Primary Examiner* — Allen C. Ho
(74) *Attorney, Agent, or Firm* — Sughrue Mion, PLLC

(57) ABSTRACT

Provided are a radiographic imaging apparatus and a method of controlling the same. The radiographic imaging apparatus includes a radiographic source configured to emit radiographic rays in a discontinuous eigen energy spectrum, a radiographic detector configured to receive the radiographic rays, convert the received radiographic rays into electrical signals, and count the number of photons having energy that exceeds a threshold energy, and a controller configured to adjust the threshold energy by comparing an energy spectrum of the detected radiographic rays with the eigen energy spectrum of the emitted radiographic rays from the radiographic source.

20 Claims, 20 Drawing Sheets

(52) U.S. Cl.
CPC ............. A61B 6/582 (2013.01); G01N 23/087 (2013.01); G01T 7/00 (2013.01); G01T 7/005 (2013.01); *A61B 6/032* (2013.01); *A61B 6/4452* (2013.01); *A61B 6/4464* (2013.01); *G01N 2223/205* (2013.01)

(58) Field of Classification Search
USPC ................ 378/5, 9, 16, 19, 98.8, 98.9, 207; 250/252.1, 370.09
See application file for complete search history.

(56) References Cited

U.S. PATENT DOCUMENTS

| | | | | |
|---|---|---|---|---|
| 5,943,388 A * | 8/1999 | Tumer | ................. | G01V 5/0041 378/98.11 |
| 7,479,639 B1 * | 1/2009 | Shahar | ...................... | G01T 1/17 250/370.06 |
| 7,696,483 B2 * | 4/2010 | Tkaczyk | ................. | G01T 1/171 250/370.06 |
| 7,902,976 B2 * | 3/2011 | Doughty | ................. | G01T 1/026 250/370.1 |
| 7,983,397 B2 * | 7/2011 | Michel | .................... | G01T 1/026 250/370.07 |
| 8,585,286 B2 * | 11/2013 | Livne | ..................... | A61B 6/032 378/207 |
| 8,941,076 B2 * | 1/2015 | Abraham | ................ | G01T 1/171 250/336.1 |
| 8,985,853 B2 * | 3/2015 | Lee | .......................... | G01T 7/005 378/207 |
| 2011/0210262 A1 * | 9/2011 | Prendergast | ............ | G01T 1/247 250/394 |

* cited by examiner

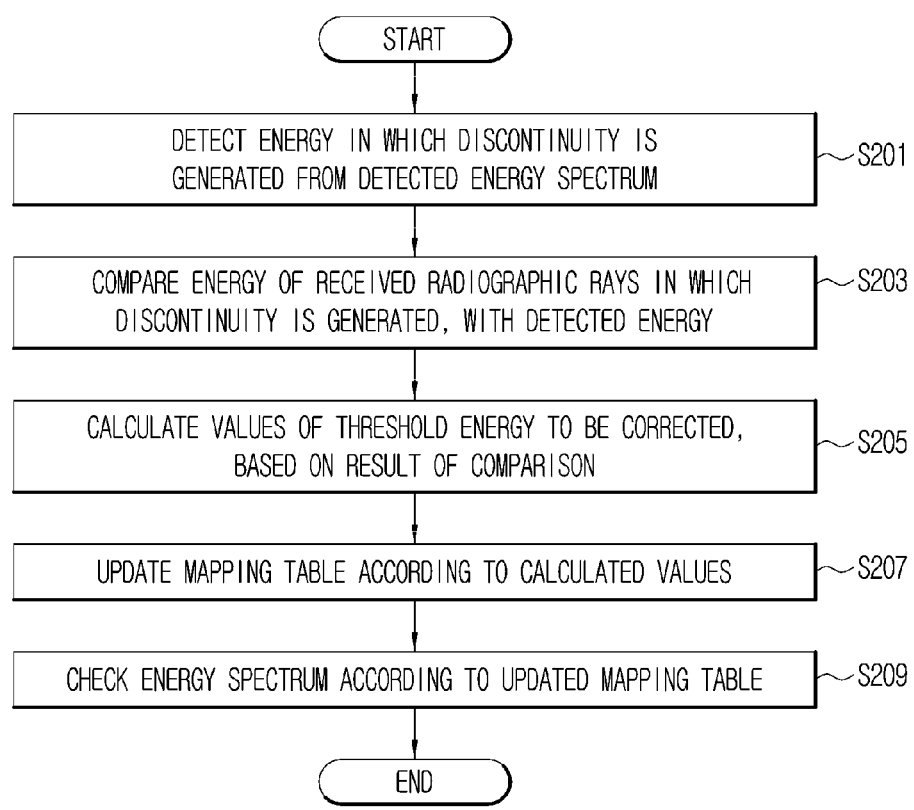

RADIOGRAPHIC IMAGING APPARATUS AND A METHOD OF CORRECTING THRESHOLD ENERGIES IN A PHOTON-COUNTING RADIOGRAPHIC DETECTOR

CROSS-REFERENCE TO RELATED APPLICATION

This application claims priority from Korean Patent Application No. 10-2013-0143788, filed on Nov. 25, 2013 in the Korean Intellectual Property Office, the disclosure of which is incorporated herein by reference in its entirety.

BACKGROUND

1. Field

Apparatuses and methods consistent with exemplary embodiments relate to a radiographic imaging apparatus that is capable of generating a radiographic image by radiating radiographic rays onto an object and using the collected radiographic rays transmitted through the object and a method of controlling the same.

2. Description of the Related Art

Radiographic imaging apparatuses are apparatuses that are capable of obtaining an image inside an object by radiating radiographic rays onto an object and using the collected radiographic rays transmitted through the object. Because transmittance of the radiographic rays varies according to the characteristics of a material used to form the object, an internal structure of the object can be imaged by detecting an intensity and/or strength of the collected radiographic rays transmitted through the object.

In detail, when the radiographic rays are generated by a radiographic generator and are radiated onto the object, a radiographic detector detects the radiographic rays transmitted through the object and converts the detected radiographic rays into electrical signals. Because conversion of the electrical signals is performed in each pixel, the electrical signals corresponding to the pixels may be combined with each other so as to obtain one radiographic image.

In the related art, a method of accumulating electrical signals for a predetermined amount of time and reading the electrical signals has been mainly used. However, a photon counting detector (PCD) that counts photons having predetermined energy or more and separates detected radiographic rays according to energy has been recently developed.

The PCD has advantages such as, for example, the PCD can separate a particular material from a radiographic image and has less radiation exposure and less noise. However, even when radiographic rays having the same energy are incident onto all pixels due to the effects caused by characteristics of a light receiving device or a read-out circuit according to pixels, different counter values may be output according to pixels, which causes noise in an image.

SUMMARY

According to an aspect of an exemplary embodiment, there is provided a radiographic imaging apparatus including a radiographic source configured to emit radiographic rays in a discontinuous eigen energy spectrum, a radiographic detector configured to receive the radiographic rays, convert the received radiographic rays into electrical signals, and count the number of photons having energy that exceeds a threshold energy, and a controller configured to adjust the threshold energy by comparing an energy spectrum of the detected radiographic rays with the eigen energy spectrum of the emitted radiographic rays from the radiographic source.

The radiographic source may include at least one radiographic isotope.

The radiographic isotope may be at least one selected from the group consisting of americium-241, cadmium-109, and cobalt-57.

The radiographic source may further include a shielding unit configured to shield the radiographic rays.

The shielding unit may be further configured to guide the radiographic rays along a radiation direction.

The controller may include a spectrum generator configured to detect an energy spectrum according to pixels by varying the threshold energy, a comparator configured to compare the discontinuous eigen energy spectrum with the detected energy spectrum, and a correction unit configured to adjust the threshold energy based on a result of comparison from the comparator according to the pixels.

The controller may further include a mapping table in which values of the threshold energy are configured to be stored according to the pixels, and wherein the correction unit is further configured to update the mapping table according to the corrected threshold energy.

The controller may further include a testing unit configured to set threshold energy of the pixels according to the updated mapping table and determine whether errors of the pixels are within a predetermined range.

The radiographic imaging apparatus may further include a movement unit that moves the radiographic source so that the radiographic rays emitted from the radiographic source are uniformly radiated onto the radiographic detector.

The radiographic isotope may be one selected from the group consisting of a dot-shaped radiographic source, a line-shaped radiographic source, and a face-shaped radiographic source.

According to an aspect of another exemplary embodiment, there is provided a method of controlling a radiographic imaging apparatus, the method including detecting, using a radiographic detector, an energy spectrum of radiographic rays in a discontinuous energy spectrum, and adjusting, using a controller, a threshold energy by comparing the detected energy spectrum with an eigen energy spectrum of the radiographic rays.

Detecting the energy spectrum may include varying the threshold energy at predetermined intervals, and monitoring the number of photons counted in pixels.

Adjusting of the threshold energy may include calculating a difference value between the discontinuous eigen energy spectrum, with the detected energy spectrum, and determining threshold energy of the pixels based on the difference value.

Determining of the threshold energy may include determining the threshold energy of the pixels by substituting the difference value for a parameter of a predetermined function.

The adjusting of the threshold energy may include updating a mapping table in which the threshold energy is stored according to the pixels.

The adjusting of the threshold energy may further include checking whether errors of the pixels are within a predetermined range, by setting the threshold energy according to the updated mapping table.

The method may further include counting the number of photons included in the radiographic rays transmitted by an object based on the corrected threshold energy, and generating a radiographic image based on the counted number of photons.

BRIEF DESCRIPTION OF THE DRAWINGS

These and/or other aspects will become apparent and more readily appreciated from the following description of the exemplary embodiments, taken in conjunction with the accompanying drawings of which:

FIG. 16 is a flowchart illustrating a method of correcting threshold energy according to an exemplary embodiment.

Figure 1:
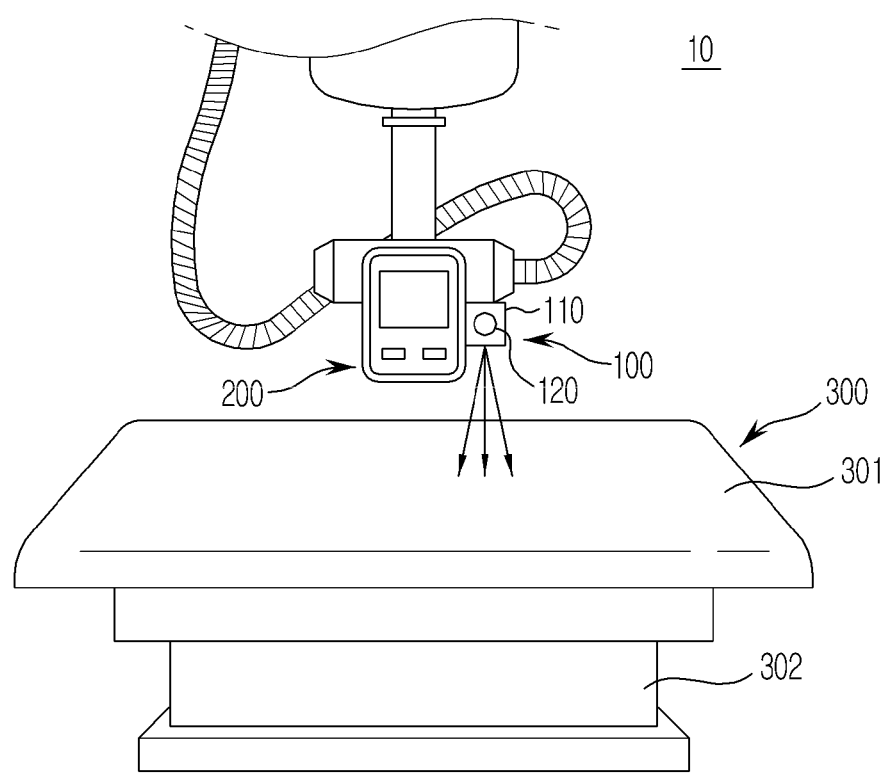
FIG. 1 is a perspective view of a radiographic imaging apparatus according to an exemplary embodiment.

Below, exemplary embodiments will be described in detail with reference to accompanying drawings so as to be easily realized by a person having ordinary knowledge in the art. The exemplary embodiments may be embodied in various shapes without being limited to the exemplary embodiments set forth herein. Descriptions of well-known parts are omitted for clarity, and like reference numerals refer to like elements throughout.

DETAILED DESCRIPTION

Below, exemplary embodiments will be described in detail with reference to accompanying drawings so as to be easily realized by a person having ordinary knowledge in the art. The exemplary embodiments may be embodied in various shapes without being limited to the exemplary embodiments set forth herein. Descriptions of well-known parts are omitted for clarity, and like reference numerals refer to like elements throughout.

Figure 2:
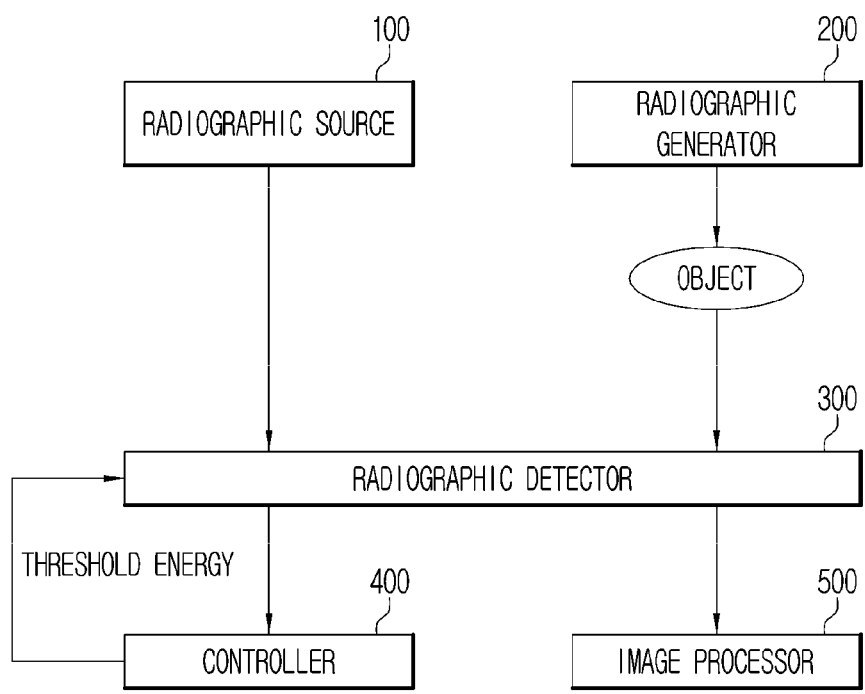
FIG. 2 is a control block diagram of an radiographic imaging apparatus, similar to that illustrated in FIG. 1, according to an exemplary embodiment.

FIG. 1 is a perspective view of a radiographic imaging apparatus according to an exemplary embodiment, and FIG. 2 is a control block diagram of a radiographic imaging apparatus similar to that illustrated in FIG. 1 according to an exemplary embodiment.

Referring to FIGS. 1 and 2, a radiographic imaging apparatus 10 may include a radiographic source 100, a radiographic generator 200, a radiographic detector 300, a controller 400, and an image processor 500.

The radiographic source 100 may emit radiographic rays having a discontinuous energy spectrum. The radiographic rays that are emitted from the radiographic source 100, and have the discontinuous energy spectrum, may be used to correct threshold energy. Additionally, the radiographic source 100 may include a shielding unit 110 and a radiographic isotope 120.

The shielding unit 110 adjusts radiation of the radiographic rays emitted from the radiographic isotope 120. Particularly, the shielding unit 110 may block the radiographic rays emitted from the radiographic isotope 120 so that they are not emitted to the outside and/or may guide a radiographic radiation direction or radiation range. To this end, the shielding unit 110 may include a collimator filter or collimator blade formed of a material that absorbs the radiographic rays, for example, metal, such as lead (Pb), tungsten (W), or molybdenum (Mo).

The radiographic isotope 120 emits the radiographic rays having the discontinuous energy spectrum. In this case, the radiographic isotope 120 emits the radiographic rays by converting the radiographic rays to have a state in which an atomic nucleus is stabilized. For example, the radiographic isotope 120 may be americium-241 (Am-241), cadmium-109 (Cd-109), or cobalt-57 (Co-57). The radiographic source 100 may include at least one radiographic isotope 120.

In more detail, distribution of energy of the radiographic rays emitted by the radiographic isotope 120 is discontinuous. Hereinafter, the discontinuous spectrum of the radiographic isotope 120 will be described in detail with reference to FIG. 3.

Figure 3A:
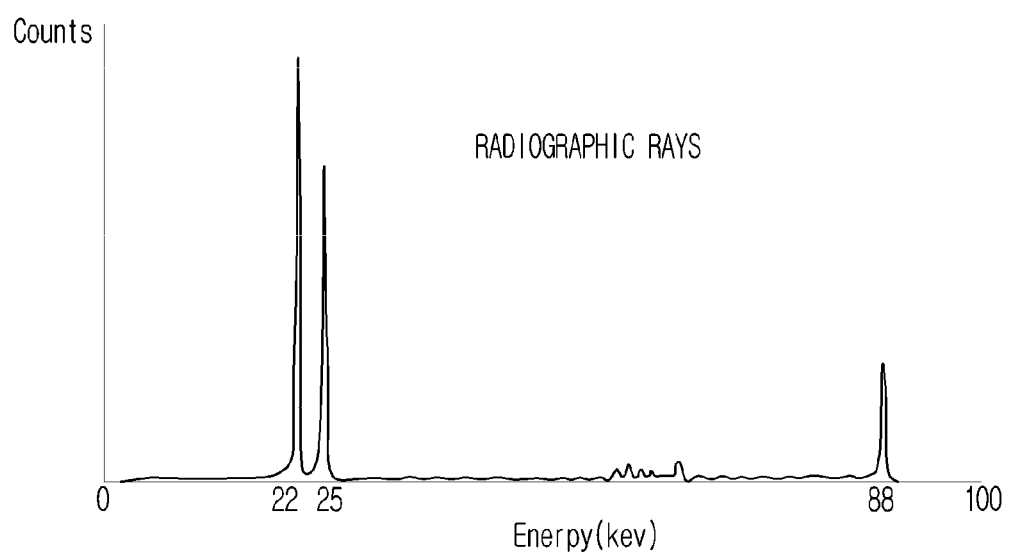
FIGS. 3A and 3B are graphs showing an example of an eigen energy spectrum of radiographic rays emitted from a radiographic source according to one or more exemplary embodiments.
Figure 3B:
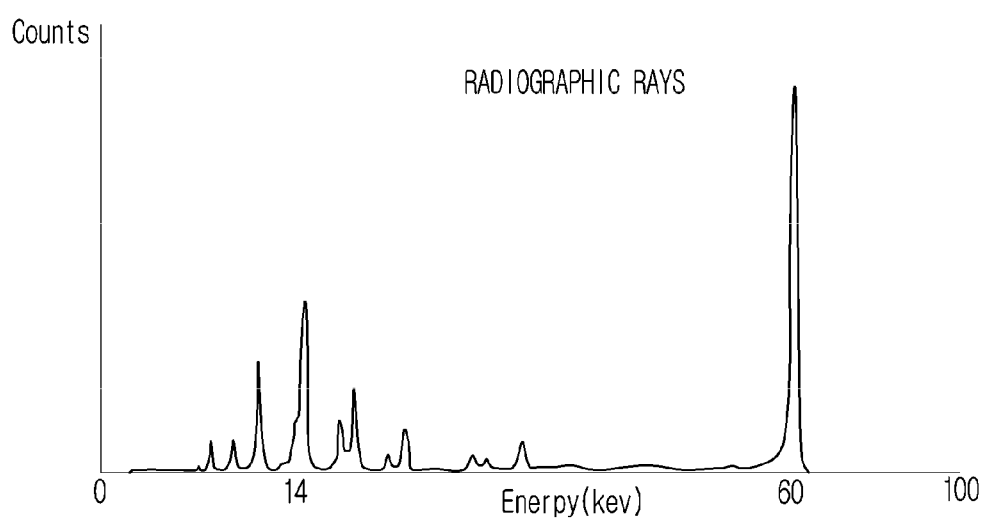

FIGS. 3A and 3B are graphs showing an example of an eigen energy spectrum of radiographic rays emitted from a radiographic source. FIG. 3A illustrates an energy spectrum of Cd-109. FIG. 3B illustrates an energy spectrum of Am-241. In this case, a horizontal axis of each of FIGS. 3A and 3B represents energy of photons keV, and a vertical axis thereof represents the number of photons each having energy.

Referring to FIG. 3A, most parts of photons emitted from Cd-109 have particular energy. Particularly, about 80% of photons emitted from Cd-109 have energy of 22 keV, and about 15% of the photons emitted from Cd-109 have energy of 25 keV, and about 4% of the photons emitted from Cd-109 have energy of 88 keV. That is, when the photons emitted from Cd-109 are classified according to energy, the photons are represented as the discontinuous energy spectrum shown in FIG. 3A. In this case, the number of the photons increases rapidly and then is reduced at energy of 22 keV, 25 keV, and 88 keV. In other words, the number of the photons detected at energy of 22 keV, 25 keV, and 88 keV increases rapidly compared to other energy bands.

Referring to FIG. 3B, most parts of photons emitted from Am-241 have particular energy. In more detail, about 42% of the photons emitted from Am-241 have energy of 14 keV, and about 2.4% of the photons have energy of 26 keV, and about 35.9% of the photons have energy of 60 keV. That is, when the photons emitted from Am-241 are classified according to energy, the photons are represented as the discontinuous energy spectrum shown in FIG. 3B. In this case, the number of the photons increases rapidly and then is reduced at energy of 14 keV, 26 keV, and 60 keV.

The discontinuous energy spectrum of the radiographic isotope 120 may be used as a reference for correcting threshold energy of the controller 400 that will be described below.

It will be understood that the radiographic isotope 120 is not interpreted to be limited to Cd-109 or Am-241 and may include all of the radiographic isotopes 120 having the discontinuous energy spectrum, such as Co-57.

Referring back to FIGS. 1 and 2, the radiographic generator 200 may generate radiographic rays and radiate the generated radiographic rays onto an object. The radiographic generator 200 may generate the radiographic rays with supplied power, and energy of the radiographic rays may be controlled by a tube voltage, and an intensity or a radiation dose of the radiographic rays may be controlled by a tube current and a radiographic exposure time. Hereinafter, the radiographic generator 200 will be described in more detail with reference to FIG. 4.

Figure 4:
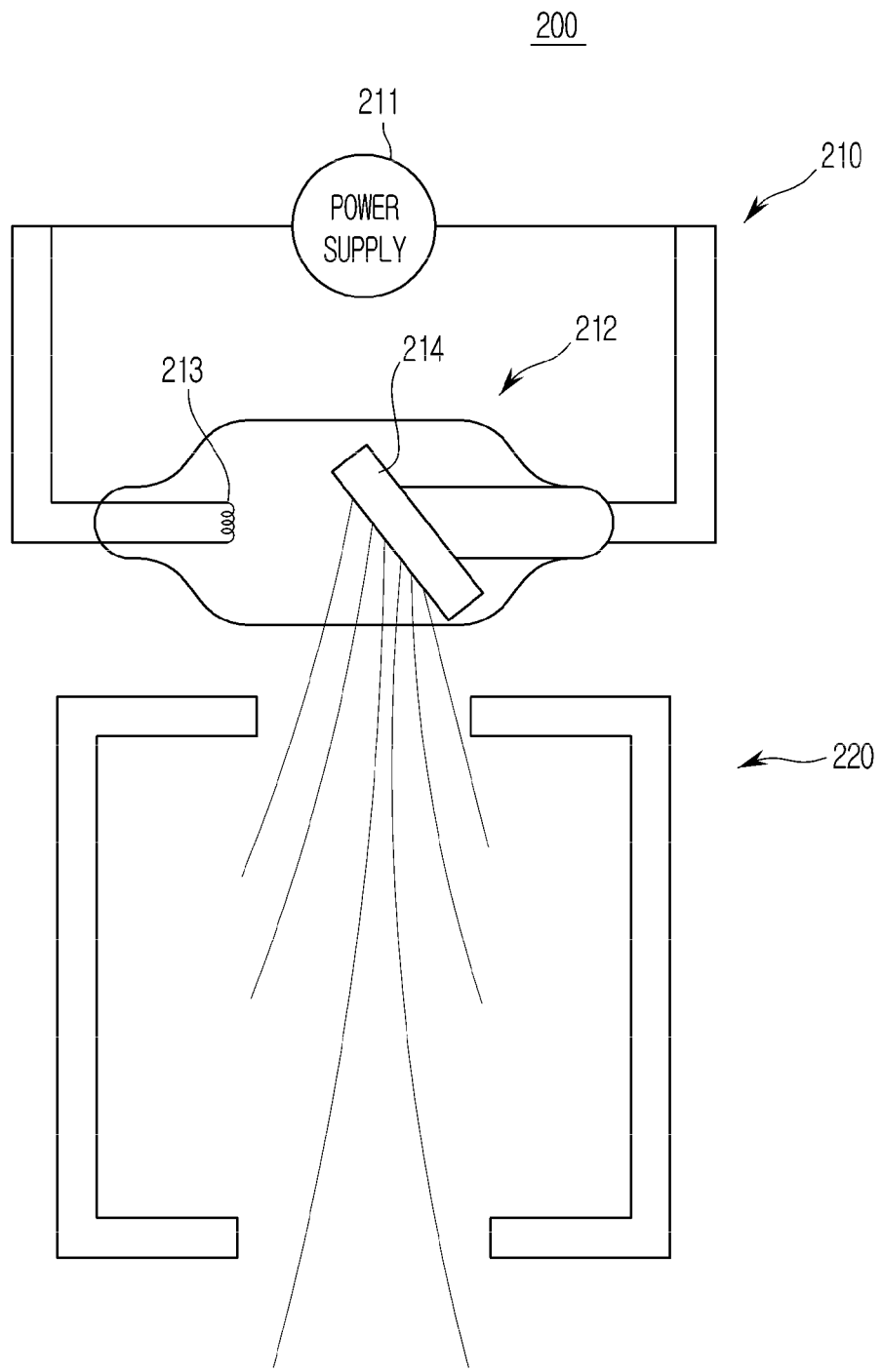
FIG. 4 illustrates a radiographic generator according to an exemplary embodiment.

FIG. 4 illustrates a radiographic generator according to an exemplary embodiment.

Referring to FIG. 4, the radiographic generator 200 may include a sub radiographic generator 210 and a collimator 220.

The sub radiographic generator 210 may include a power supply 211 for providing a voltage, and a radiographic tube (cathode ray tube) 212 that may generate radiographic rays having an energy level corresponding to the applied voltage.

The power supply 211 is electrically connected to the radiographic tube 212 and applies a predetermined voltage to the radiographic tube 212 according to an external control instruction.

The radiographic tube 212 includes a cathode filament 213 and an anode 214. When the predetermined voltage is applied to the radiographic tube 212 from the power supply 211, electrons of the cathode filament 213 of the radiographic tube 212 are accelerated in a direction of the anode 214 and move to the anode 214. As the accelerated electrons are rapidly decelerated by a Coulomb force in the vicinity of the anode 214, predetermined radiographic rays, for example X-rays, are generated in the anode 214 according to the principle of the conservation of energy.

In this case, an energy amount, i.e., an energy level of the radiographic rays generated in the radiographic tube 212 is determined according to the voltage applied from the power supply 211. For example, when a low voltage is applied to both ends of the radiographic tube 212, electrons in the radiographic tube 212 are relatively slowly accelerated and thus, radiographic rays having low energy are generated in the anode 214. In contrast, when a high voltage is applied to the radiographic tube 212, the electrons in the radiographic tube 212 are quickly accelerated and thus, radiographic rays having high energy are generated in the anode 214. The radiographic rays generated in the anode 214 of the radiographic tube 212 may be radiated in a predetermined direction, as illustrated in FIG. 4, for example, in a direction of the radiographic detector 300.

The radiographic rays generated by the sub radiographic generator 210 may first pass through the collimator 220 before being radiating onto the radiographic detector 300.

The collimator 220 that is a device for guiding a radiographic radiation direction or radiation range may block the radiographic rays by absorbing the radiographic rays radiated in directions other than a desired direction so as to determine the radiation direction or range of the radiographic rays. To this end, the collimator 220 may include a collimator filter or collimator blade formed of a material that absorbs the radiographic rays, for example, metal, such as lead Pb.

Referring back to FIG. 1, the radiographic detector 300 may include a holder 301 on which an object, such as a human body, may be held, as illustrated in FIG. 1, and a support 302 that supports the holder 301.

The radiographic detector 300 may detect the radiographic rays and convert the detected radiographic rays into electrical signals, thereby obtaining radiographic data for generating a radiographic image. In more detail, the radiographic detector 300 may receive the radiographic rays and count the number of photons having energy that exceeds threshold energy among the photons included in the received radiographic rays according to pixels, thereby obtaining data for generating a radiographic image.

In general, the radiographic detector 300 may be classified according to a material composition method, a method of converting detected radiographic rays into electrical signals, and a method of obtaining radiographic data. Hereinafter, various methods, whereby the radiographic detector 300 detects radiographic rays and converts the detected radiographic rays into electrical signals, thereby obtaining radiographic data, will be described.

First, the radiographic detector 300 may be classified into a case where the radiographic detector 300 is configured as a single type device, and a case where the radiographic detector 300 is configured as a mixed type device, according to the material composition method.

When the radiographic detector 300 is configured as the single type device, a portion of the radiographic detector 300 for detecting the radiographic rays and generating electrical signals and a portion of the radiographic detector 300 for reading and processing the electrical signals may be formed as a semiconductor formed of a single material or manufactured with a single process, for example, using only a charge coupled device (CCD) that is a light receiving device or a complementary metal oxide semiconductor (CMOS).

When the radiographic detector 300 is configured as the mixed type device, the portion of the radiographic detector 300 for detecting the radiographic rays and generating electrical signals and the portion of the radiographic detector 300 for reading and processing the electrical signals may be formed of different materials or manufactured with different processes. For example, the radiographic rays may be detected using a light receiving device, such as a photodiode, a CCD, or CdZnTe, and the electrical signals may be read and processed using a CMOS read out integrated circuit (ROIC), or the radiographic rays may be detected using a strip detector, and the electrical signals may be read and processed using the CMOS ROIC, or an a-Si or a-Se flat panel system may be used.

The radiographic detector 300 may be classified into a direct conversion method and an indirect conversion method according to a method of converting radiographic rays into electrical signals.

In the direct conversion method, when the radiographic rays are detected, pairs of electrons and holes are temporarily generated in a light receiving device, and electrons are moved to an anode, and holes are moved to a cathode due to an electric field applied to both ends of the light receiving device. Thus, the radiographic detector 300 converts the movement into electrical signals. In the direct conversion method, a-Se, CdZnTe, HgI$_2$, PbI$_2$, or the like may be used to form the light receiving device.

In the indirect conversion method, when a scintillator is provided between a light receiving device and the radiographic generator 200 and the scintillator reacts with the radiographic rays radiated by the radiographic generator 200 and emits photons having a wavelength in a visible light region, the light receiving device detects the photons emitted from the scintillator and converts the detected photons into electrical signals. In the indirect conversion method, a-Si may be used to form the light receiving device, and a gadolinium oxysulfide (GADOX) scintillator having a thin film shape or a micro pillar-shaped or needle-shaped CSI (TI) scintillator may be used to form the scintillator.

Also, the radiographic detector 300 may be classified according to a method of obtaining radiographic data by a charge integration mode in which charges are stored for a predetermined amount of time and then signals are obtained from the charges or a photon counting mode in which photons having energy that exceeds threshold energy are counted whenever a signal is generated from single radiographic photons.

In an exemplary embodiment of the radiographic imaging apparatus 10, the photon counting mode having less radiation dose of radiographic rays with respect to the object and less noise of the radiographic image compared to the charge integration mode is used. Thus, the radiographic detector 300 is implemented as a photon counting detector (PCD).

There are no limitations in the material composition method and the method of converting of detected radiographic rays into electrical signals of the radiographic detector 300. However, for convenience of explanation, the following detailed exemplary embodiments will now be described using the direct conversion method, whereby electrical signals are directly obtained from radiographic rays, and a hybrid method, whereby a light receiving device for detecting radiographic rays and a read-out circuit are combined with each other.

Figure 5:
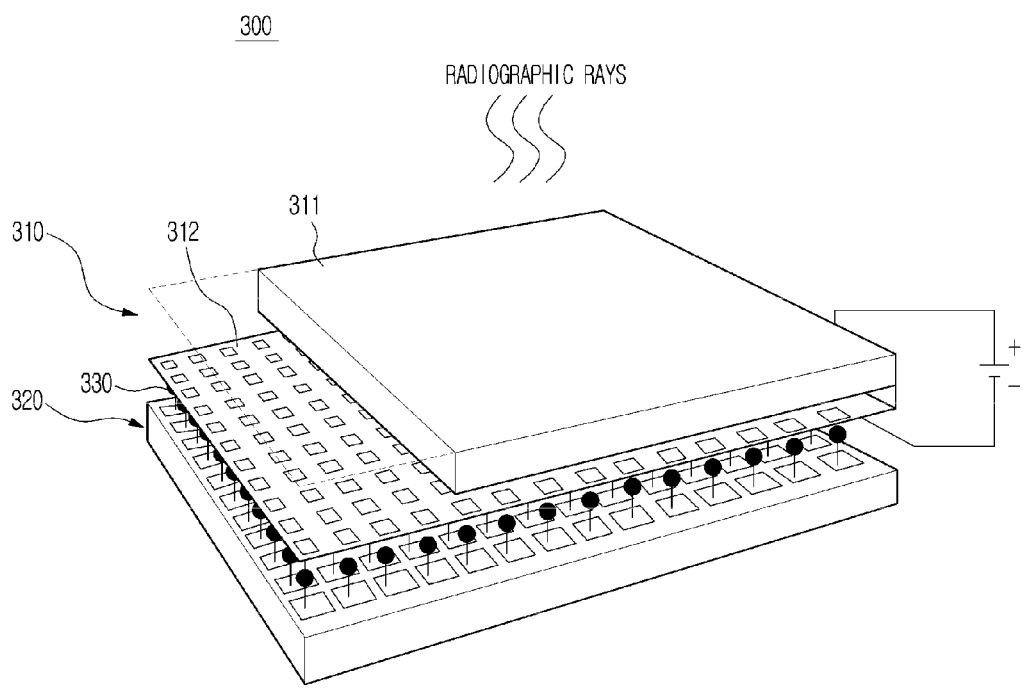
FIG. 5 schematically illustrates a structure of a radiographic detector of an radiographic imaging apparatus, similar to that illustrated in FIG. 1, according to an exemplary embodiment.
Figure 6:
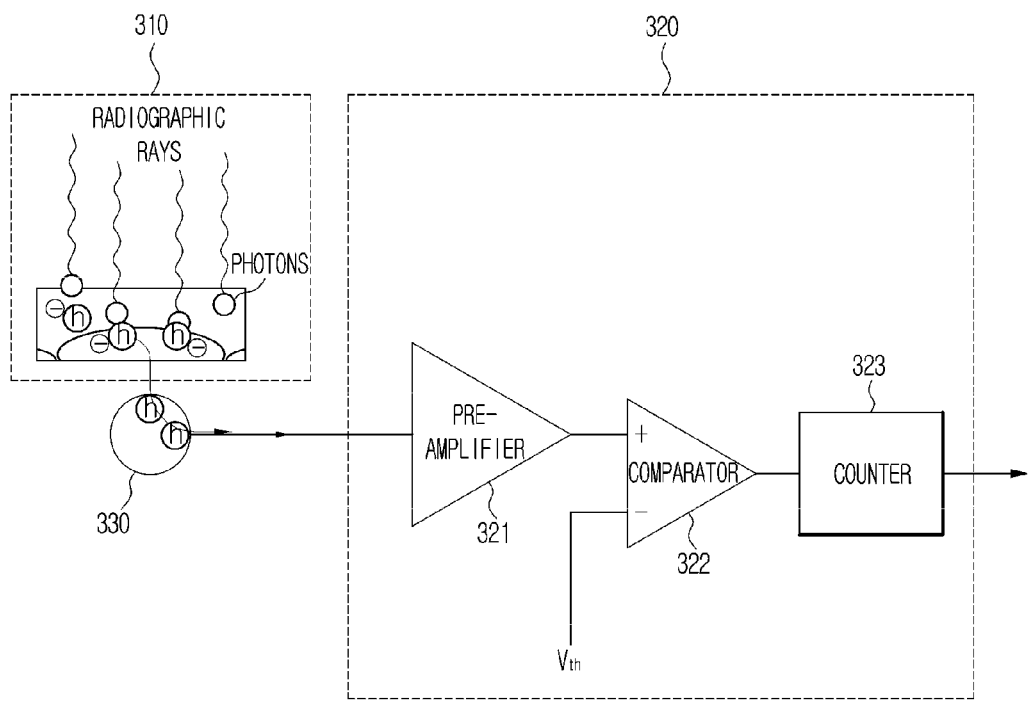
FIG. 6 schematically illustrates a single pixel region of an radiographic detector.
Figure 7:
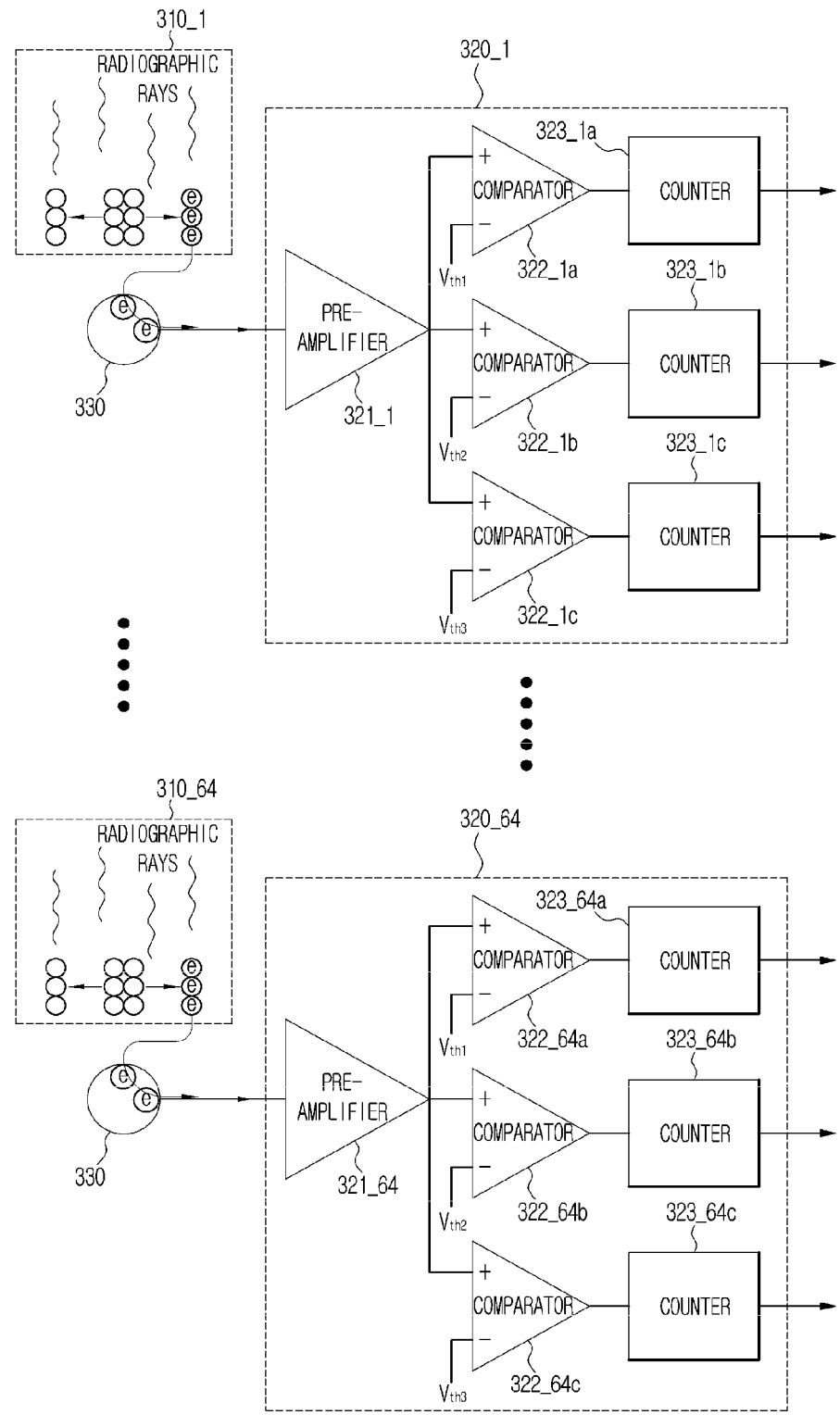
FIG. 7 schematically illustrates a radiographic detector that may separate radiographic rays according to a plurality of energy bands according to an exemplary embodiment.

FIG. 5 schematically illustrates a structure of a radiographic detector 300 of the radiographic imaging apparatus 10 illustrated in FIG. 1. FIG. 6 schematically illustrates a single pixel region of the radiographic detector 300. FIG. 7 schematically illustrates a radiographic detector 300 that may separate radiographic rays according to a plurality of energy bands.

Referring to FIG. 5, the radiographic detector 300 includes a light receiving device 310 that detects radiographic rays and converts the detected radiographic rays into electrical signals, and a read-out circuit 320 that reads out the electrical signals. Here, the read-out circuit 320 is configured in a shape of a two-dimensional (2D) pixel array including a plurality of pixel regions. A monocrystalline semiconductor material may be used as a material used to form the light receiving device 310 so as to secure high resolution, a fast response time, and a high dynamic region at low energy and less radiation dose. The monocrystalline semiconductor material may be Ge, CdTe, CdZnTe, or GaAs.

The light receiving device 310 may be configured in a shape of a PIN photodiode by bonding a p-type layer 312 in which a p-type semiconductor is arranged in a structure of the 2D pixel array, to a lower portion of an n-type semiconductor substrate 311 having a high resistance, and the read-out circuit 320 using a CMOS process is combined with the light receiving device 310 according to pixels.

Because the CMOS read-out circuit 320 and the light receiving device 310 can be combined with each other in a flip chip bonding manner, they can be combined with each other by forming a bump bonding 330 using a material, such as a tin/lead solder (PbSn) or indium (In), and then reflowing, heating, and compressing the bump. However, the above-described structure is merely an exemplary embodiment of the radiographic detector 300, and the structure of the radiographic detector 300 is not limited thereto.

Referring to FIG. 6, when photons of the radiographic rays are incident on the light receiving device 310, electrons that are present in a valence band receive energy of the photons and are excited into a conduction band beyond a difference in bandgap energy. Thus, pairs of electrons and holes are generated in a depletion region.

When a metal electrode is formed on each of the p-type layer 312 and the n-type semiconductor substrate 311 of the light receiving device 310 and a reverse bias voltage is applied to the metal electrode, electrons of the pairs of electrons and holes generated in the depletion region are dragged into an n-type region, and holes of the pairs of electrons and holes are dragged into a p-type region. The holes dragged into the p-type region are input to the read-out circuit 320 through bump bonding 330 so that the read-out circuit 320 can read electrical signals generated by the photons. However, the electrons may be input to the read-out circuit 320, and the electrical signals may be generated according to the structure of the light receiving device 310 and a voltage applied to the light receiving device 310.

The read-out circuit 320 may be formed in the structure of the 2D pixel array that corresponds to the p-type layer 312 of the light receiving device 310 and reads the electrical signals according to pixels. When charges are input to the read-out circuit 320 from the light receiving device 310 through the bump bonding 330, a pre-amplifier 321 of the read-out circuit 320 charges the input charges generated from one photon and outputs voltage signals corresponding to the charges.

The voltage signals output from the pre-amplifier 321 are transferred to a comparator 322. The comparator 322 compares threshold voltages Vth that may be controlled by an external device, with the input voltage signals and outputs a pulse signal of '1' or '0' according to a result of comparison. A counter 323 counts the number of times in which '1' is output, and outputs radiographic data in a digital format. When pieces of radiographic data are combined with each other according to pixels, an X-ray image of the object to be examined can be obtained.

Here, the threshold voltages Vth correspond to threshold energy. When the number of photons having energy of E or more is counted, threshold voltages Vth corresponding to threshold energy E are input to the comparator 322. The threshold voltages Vth may correspond to threshold energy, because magnitudes of the electrical signals (voltages) generated in the light receiving device 310 vary according to energy of the photons. Thus, the threshold voltages Vth corresponding to desired threshold energy may be calculated using an equation that shows the relationship between energy of photons and generated voltages, and threshold energy input to the radiographic detector 300 in the following exemplary embodiment may mean threshold voltages Vth corresponding to threshold energy input to the radiographic detector 300.

The radiographic imaging apparatus 10 may obtain a radiographic image in a plurality of different energy bands and generate a multi-energy radiographic image so as to improve contrast between internal tissues of the object. To this end, the radiographic imaging apparatus 10 may radiate the radiographic rays a plurality of times by varying radiographic bands so as to obtain an X-ray image in a plurality of different energy bands.

However, in an exemplary embodiment of the radiographic imaging apparatus 10, the radiographic detector 300 may separate photons of the received radiographic rays using the read-out circuit 320 illustrated in FIG. 7 according to a plurality of energy bands.

In more detail, the read-out circuit 320 may count the number of photons according to the plurality of energy bands by comparing a plurality of comparators 322 and a plurality of counters 323. In FIG. 7, three comparators are provided. However, the exemplary embodiment of the radiographic detector 300 is not limited thereto, and the number of comparators corresponding to the number of energy bands to be separated may also be provided.

When the radiographic detector 300 is composed of 64 pixels, the radiographic detector 300 may include 64 light receiving devices 310_1 through 310_64, and 64 read-out circuits 320_1 through 320_64, as illustrated in FIG. 7.

Referring to FIG. 7, when photons of the radiographic rays are incident on the light receiving device 310, many pairs of electrons and holes are generated by receiving energy of the photons. In this case, the number of the generated pairs of electrons and holes is in proportional to coupling energy of the material used to form the light receiving device 310. For example, when the light receiving device 310 is formed of CdTe, as illustrated in FIG. 7, the light receiving device 310 generates a pair of electrons and holes per 4.43 eV. Thus, when photons having energy of 100 keV are incident on the light receiving device 310_1, the light receiving device 310_1 generates about 22,600 pairs of electrons and holes.

The electrons of the pairs of electrons and holes generated by the photons of the radiographic rays are moved to an anode and are input to the read-out circuit 320 through the bump bonding 330 so that the electrical signals generated by the photons can be read. The electrons may be input to the read-out circuit 320, and the electrical signals may be generated according to the structure of the light receiving device 310 or a voltage applied to the light receiving device 310.

For example, when the photons of the radiographic rays are received by the light receiving device 310_1, electrical signals are generated by the electrons generated by the received photons, and a pre-amplifier 321_1 amplifies the electrical signals generated by the light receiving device 310_1 and outputs the amplified electrical signals.

The electrical signals output by the pre-amplifier 321_1 in this way are input to three comparators 322_1a, 322_1b, and 322_1c. When first through third threshold voltages Vth1 through Vth3 are input to the comparators 322_1a, 322_1b, and 322_1c, the comparator 322_1a compares the first threshold voltage Vth1 with an input voltage, and a first counter 323_1a counts the number of photons that generate a greater voltage than the first threshold voltage Vth1. In the same way, a second counter 323_1b counts the number of photons that generate a greater voltage than the second threshold voltage Vth2, and a third counter 323_1c counts the number of photons that generate a greater voltage than the third threshold voltage Vth3.

Even though, in theory, magnitudes of the voltage signals generated in pixels of the radiographic detector 300 may be affected only by energy of the incident photons, the magnitudes of the voltage signals may also be affected by characteristics of the light receiving device 310 or the read-out circuit 320 of each of the pixels. Thus, even when photons having the same energy are incident on all of the pixels, the magnitudes of the voltage signals generated in a single photon may vary according to pixels. Hereinafter, this will be described with reference to FIGS. 7 through 8 in more detail.

Figure 8A:
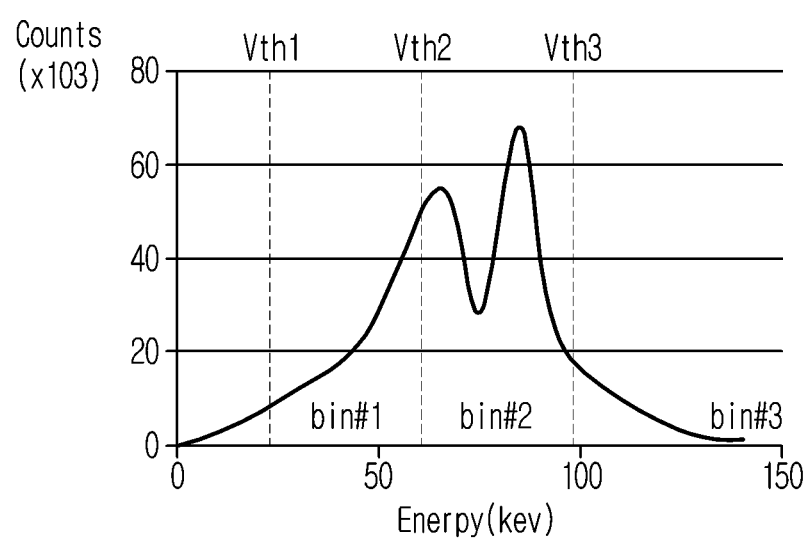
FIGS. 8A and 8B are graphs illustrating threshold energy correction according to one or more exemplary embodiments.
Figure 8B:
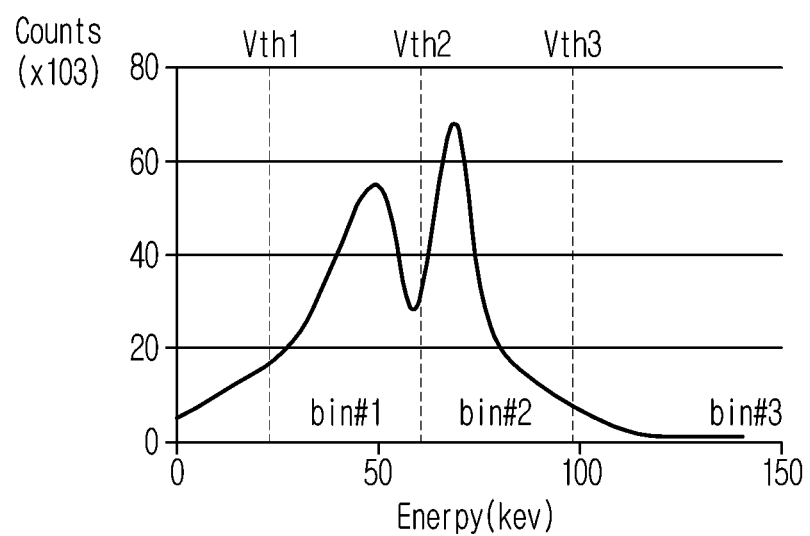

FIGS. 8A and 8B are graphs illustrating the need to correct threshold energy.

Even when photons having the same energy are received in pixels of one radiographic detector 300, energy spectrums detected in the pixels may be different from each other, as illustrated in FIGS. 8A and 8B.

Referring to FIGS. 7, 8A, and 8B, when photons having the energy spectrum of FIG. 8A are received in the pixels, the photons are input to the pre-amplifier 321_1 and are output as voltage signals, and the voltage signals are input to three comparators 322_1a, 322_1b, and 322_1c, and the comparators 322_1a, 322_1b, and 322_1c compare the first through third threshold voltages Vth1, Vth2, and Vth3 with energy of the photons, and the first through third counters 323_1a, 323_1b, and 323_1c count the number of photons that are greater than the first through third threshold voltages Vth1, Vth2, and Vth3.

Thus, ideally, many photons are counted in the pixels in the order of a second energy region bin #2, a first energy region bin #1, and a third energy region bin #3.

However, even when photons having the same energy spectrum as that of FIG. 8A are received in the pixels, voltage signals generated in the photons according to the characteristics of the light receiving device 310 or the read-out circuit 320 may be interpreted that photons having the same energy spectrum as that of the FIG. 8B are received.

Thus, many photons are counted in pixels to be corrected, in the order of the first energy region bin #1, the second energy region bin #2, and the third energy region bin #3. That is, errors occur in the number of photons of each energy region detected by the radiographic detector 300. Thus, errors occur in the radiographic image.

Referring back to FIG. 2, the controller 400 generates an energy spectrum according to the pixels by controlling the radiographic detector 300 and compares the generated energy spectrum with the eigen energy spectrum emitted from the radiographic source 100 so as to correct threshold energy according to the pixels. Hereinafter, the controller 400 will be described with reference to FIGS. 9 through 11 in more detail.

Figure 9:
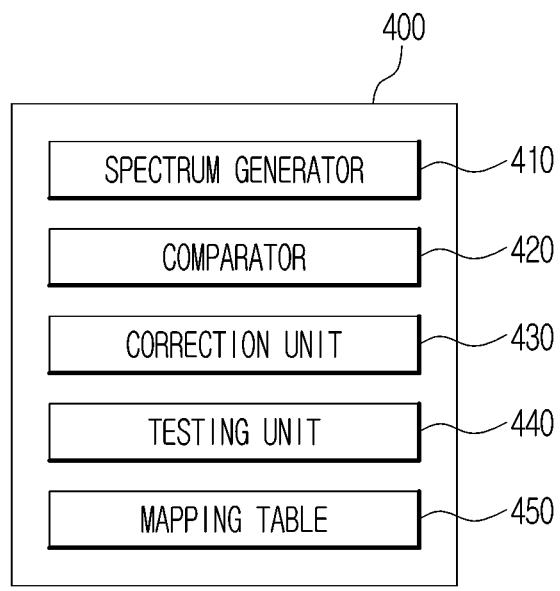
FIG. 9 is a block diagram of a controller according to an exemplary embodiment.
Figure 10A:
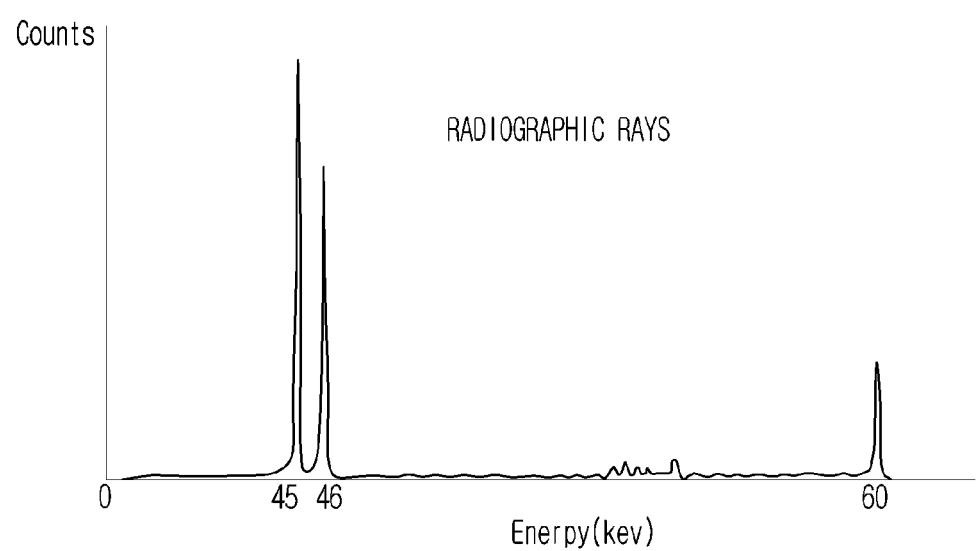
FIGS. 10A and 10B illustrate an example of an energy spectrum detected by a controller according to one or more exemplary embodiments.
Figure 10B:
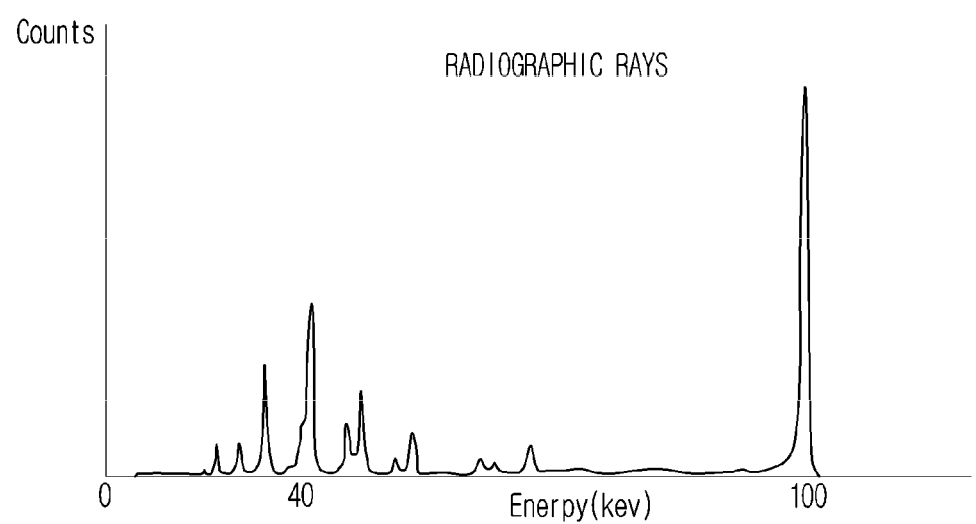
Figure 11:
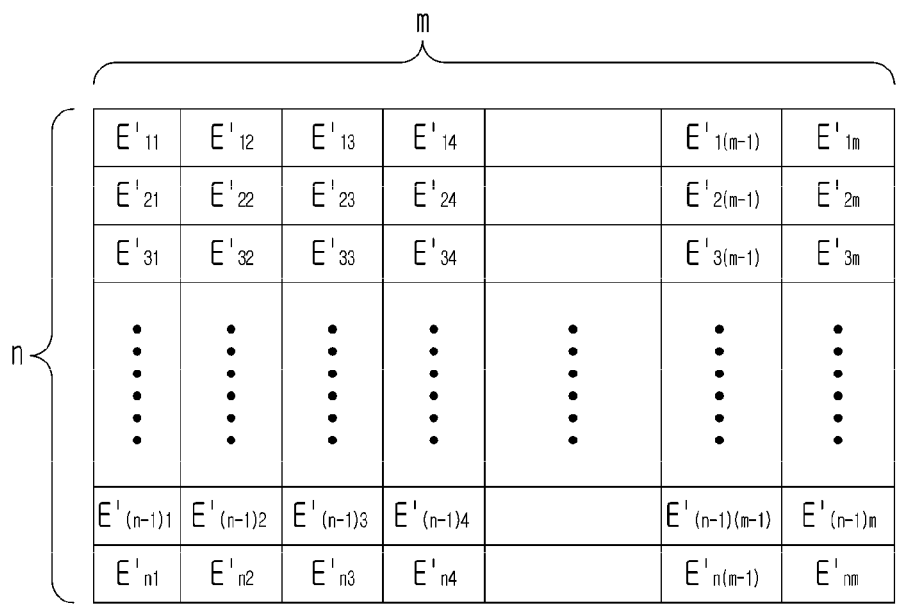
FIG. 11 schematically visualizes a mapping table according to an exemplary embodiment.

FIG. 9 is a block diagram of a controller 400 according to an exemplary embodiment. FIGS. 10A and 10B illustrate an example of an energy spectrum detected by the controller 400. FIG. 11 schematically visualizes a mapping table 450.

Referring to FIG. 9, the controller 400 may include a spectrum generator 410, a comparator 420, a correction unit 430, a testing unit 440, and a mapping table 450. Hereinafter, for convenience of explanation, the controller 400 may be configured with the spectrum generator 410, the comparator 420, the correction unit 430, the testing unit 440, and the mapping table 450. However, it will be understood that the spectrum generator 410, the comparator 420, the correction unit 430, the testing unit 440, and the mapping table 450 may be configured as one device.

The spectrum generator 410 generates an energy spectrum by varying threshold energy generated in the pixels of the radiographic detector 300. The spectrum generator 410 may monitor the number of photons counted by varying threshold energy in the pixels so as to generate energy spectrums in the pixels.

In an exemplary embodiment, the spectrum generator 410 may generate energy spectrums by storing the number of photons counted in the pixels of the radiographic detector 300 by varying threshold energy at predetermined intervals. For example, the spectrum generator 410 may store the number of photons counted according to the pixels by varying threshold energy in a unit of 5 keV and may generate energy spectrums using the stored number of photons.

In another exemplary embodiment, the spectrum generator 410 may store only threshold energy, of which the number of photons varies rapidly to a predetermined value or more, by varying threshold energy. For example, the spectrum generator 410 may generate energy spectrums by storing only an energy value in which the number of photons counted increases or is reduced by 30% or more according to pixels, by varying threshold energy in a unit of 3 keV.

In this way, minimum pieces of data that are comparable with a discontinuous energy spectrum emitted from the radiographic source 100 are stored so that a load of the controller 400 can be minimized.

For example, when radiographic rays emitted from Cd-109 are received in ideal pixels, the energy spectrum illustrated in FIG. 3A appears. Thus, when threshold energy of the pixels increases gradually, the number of photons counted in the vicinity of 22 keV, 25 keV, and 88 keV is rapidly reduced. Thus, the spectrum generator 410 may store only 22 keV, 25 keV, and 88 keV that are energy, of which the number of photons varies rapidly, as the threshold energy. Also, when a base for rapidly varying the number of photons increases, the spectrum generator 410 may store only 22 keV having a largest change in the number of photons.

Even the radiographic rays emitted from Cd-109 are received, energy spectrums detected in partial pixels may vary, as described above. For example, the energy spectrum illustrated in FIG. 10A may appear. Thus, when threshold energy of the pixels increases gradually, the number of photons counted in the vicinity of 45 keV, 46 keV, and 60 keV is rapidly reduced. Thus, the spectrum generator 410 may store 45 keV, 46 keV, and 60 keV that are energy, of which the number of photons varies rapidly, as the threshold energy.

When radiographic rays emitted from Am-241 are received in ideal pixels, the spectrum of photons illustrated in FIG. 3B appears. Thus, when threshold energy of the pixels is gradually reduced, the number of photons counted in the vicinity of 60 keV and 14 keV increases rapidly. Thus, the spectrum generator 410 may store only 60 keV and 14 keV that are energy, of which the number of photons varies rapidly, as the threshold energy.

Also, when the radiographic rays emitted from Am-241 are received, energy spectrums detected in partial pixels may vary, as described above. For example, an energy spectrum illustrated in FIG. 10B may appear. Thus, when threshold energy of the pixels is gradually reduced, the number of photons counted in the vicinity of 40 keV and 100 keV is rapidly increased. Thus, the spectrum generator 410 may store 40 keV and 100 keV, of which the number of photons counted varies rapidly, as the threshold energy.

The comparator 420 compares the discontinuous energy spectrum emitted from the radiographic source 100 with the energy spectrum generated by the spectrum generator 410. In more detail, the comparator 420 may compare energy in which discontinuity is generated from the eigen energy spectrum of the radiographic source 100, with energy in which discontinuity is generated from the spectrum generator 410.

In this case, the comparator 420 may store energy in which discontinuity is generated from the eigen energy spectrum and may also compare a stored energy value with a value in which discontinuity is generated from the energy spectrum generated by the spectrum generator 410.

Furthermore, the comparator 420 may transfer a result of comparison to the correction unit 430. For example, the comparator 420 may calculate difference values in energy in which discontinuity is generated and may store the calculated difference value in the correction unit 430. In more detail, the comparator 420 may calculate difference values 23 keV, 21 keV, and −28 keV between 22 keV, 25 keV, and 88 keV of energy in which discontinuity is generated from the eigen energy spectrum (FIG. 3A), and 45 keV, 46 keV, and 60 keV of energy in which discontinuity is generated from the energy spectrum (FIG. 10A) detected in the pixels, and may transfer the calculated difference values 23 keV, 21 keV, and −28 keV to the correction unit 430.

The correction unit 430 may correct threshold energy of the pixels based on a result transferred from the comparator 420. In more detail, the correction unit 430 may receive the difference values in which discontinuity is generated, from the comparator 420 and may correct threshold energy of the pixels based on the received different values.

In an exemplary embodiment, the correction unit 430 may linearly calculate correction values of threshold energy based on the difference values received from the comparator 420 and may correct the threshold energy according to the calculated correction values.

For example, the correction unit 430 may linearly correct a threshold energy value by comparing the eigen energy spectrum (FIG. 3A) with the detected energy spectrum (FIG. 10A). That is, the correction unit 430 may linearly correct the threshold energy value using the difference values 23 keV, 21 keV, and −28 keV received from the comparator 420 and the eigen energy spectrum. In more detail, the correction unit 430 may increase threshold energy that is adjacent to 22 keV and 25 keV by 23 keV and 21 keV that are the difference value and may reduce threshold energy that is adjacent to 60 keV by 28 keV that is the difference value.

In another exemplary embodiment, the correction unit 430 may determine a threshold energy value to be corrected, using a function in which the difference value of energy received from the comparator 420 is used as a parameter. Here, the function may be generated through experience rules or experiments.

It will be understood that the correction unit 430 may correct threshold energy using various methods other than the above-described methods.

Also, the correction unit 430 may update the mapping table 450 according to the corrected threshold energy value.

The testing unit 440 determines whether errors of the pixels are corrected based on the corrected threshold energy. In this case, when the errors of the pixels are within a predetermined range, the errors may be determined to be rightly corrected, and when the errors of the pixels are beyond the predetermined range, threshold energy correction may be performed again.

In more detail, the testing unit 440 may determine that the errors of the pixels are corrected when the number of photons counted in the pixels onto which radiographic rays are uniformly radiated from the radiographic source 100 or the radiographic generator 200, is within a predetermined range. In this case, the testing unit 440 may input threshold energy stored in the mapping table 450 as threshold energy of the pixels.

The mapping table 450 may store information regarding threshold energy to be applied according to the pixels. In this case, threshold energy information stored in the mapping table 450 may be corrected by the correction unit 430. Hereinafter, the mapping table 450 will be described with reference to FIG. 11 in more detail.

The correction unit 430 may update the mapping table 450 according to corrected threshold energy. When the radiographic detector 300 is configured of m×n pixels, the mapping table 450 may have values of threshold energy according to the pixels.

The mapping table 450 of FIG. 11 is illustrated to have one threshold energy value according to the pixels. However, when one pixel has a plurality of threshold energy, the mapping table 450 may have a structure having a plurality of threshold energy values. For example, when each pixel has three threshold energy values, as illustrated in FIG. 7, the mapping table 450 may have a structure of m×n×3.

Also, in FIG. 9, the mapping table 450 is illustrated to be included in the controller 400. However, the mapping table 450 may be provided at the radiographic detector 300. In this case, the correction unit 430 may correct values of the mapping table 450 provided at the radiographic detector 300 according to the corrected threshold energy values.

Correction of threshold energy may be performed before the radiographic imaging apparatus 10 is used, may be periodically performed, or may be performed by initialization of the radiographic imaging apparatus 10. A more precise radiographic image can be provided through threshold energy correction.

Information regarding the number of photons output by the radiographic detector 300 may be read by the image processor 500.

The image processor 500 may generate a radiographic image based on the information regarding the number of photons output by the radiographic detector 300. For example, the image processor 500 may generate a radiographic image by substituting a predetermined image value for pixels of the radiographic image corresponding to the pixels according to an intensity of radiographic rays with respect to the pixels. Specifically, when the intensity of the radiographic rays is low due to a small, little, or no number of photons counted in a predetermined pixel, the image processor 500 causes a relatively dark color, for example, black to be displayed in a pixel of the radiographic image corresponding to the predetermined pixel, and in contrast, when the intensity of the radiographic rays is high due to a large number of photons counted in the predetermined pixel, the image processor 500 causes a relatively bright color, for example, white to be displayed in a pixel of the radiographic image corresponding to the predetermined pixel so that a predetermined radiographic image can be generated.

The radiographic image generated by the image processor 500 may be stored in a storage medium, such as an additional magnetic disk or memory chip, or may be displayed on a display installed at a radiographic photographing apparatus or an external workstation.

Also, the image processor 500 may perform post-processing. For example, the image processor 500 may adjust brightness, color, contrast, or sharpness of the radiographic image, thereby further enhancing the radiographic image. The image processor 500 may generate a three-dimensional (3D) stereoscopic radiographic image.

The controller 400 or the image processor 500 of the radiographic imaging apparatus 10 may correspond to one or a plurality of processors. In this case, the processor may be implemented as an array of a plurality of logic gates or as a combination of memories in which a general-use microprocessor and a program that may be executed by the microprocessor are stored. Also, it will be understood by one of ordinary skill in the art that the processor may be implemented as hardware having other types.

Figure 12:
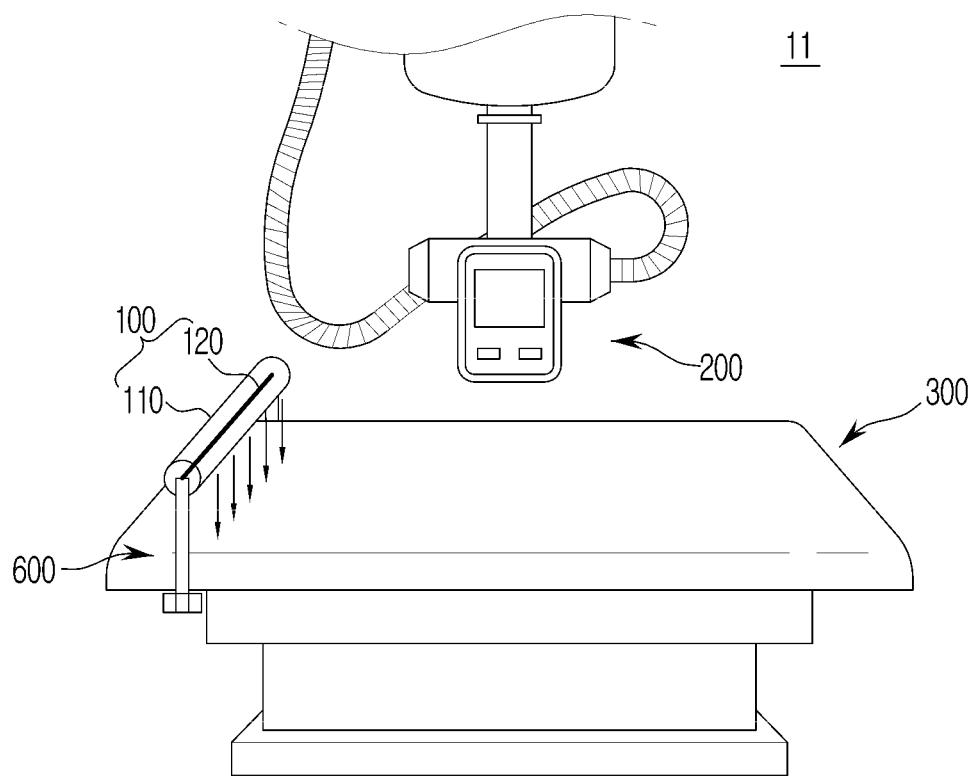
FIG. 12 is a perspective view of a radiographic imaging apparatus according to another exemplary embodiment.

FIG. 12 is a perspective view of a radiographic imaging apparatus 11 according to another exemplary embodiment.

A radiographic imaging apparatus 11 according to another exemplary embodiment has a linear radiographic source 100 so as to uniformly radiate radiographic rays. In this case, a shielding unit 110 of the radiographic source 100 may have an oval shape, and a radiographic isotope 120 may be linearly provided inside the shielding unit 110. Furthermore, the shielding unit 110 may have a door structure in which radiographic rays emitted from the radiographic isotope 120 may be radiated by the radiographic shielding unit 110 only when threshold energy is corrected.

The radiographic imaging apparatus 11 further includes a movement unit 600. The movement unit 600 may move the linear radiographic source 100 along a radiographic detector 300. In this case, the movement unit 600 may have various structures in which the linear radiographic source 100 can be moved along the radiographic detector 300. For example, the movement unit 600 may be installed to be movable along rails of an end of the radiographic detector 300 and may move the radiographic detector 300 along the rails.

In this way, the linear radiographic source 100 may move along the radiographic detector 300 and may uniformly adjust the amount of radiographic rays radiated onto each pixel of the radiographic detector 300 so that accuracy of threshold energy correction can be improved.

Figure 13:
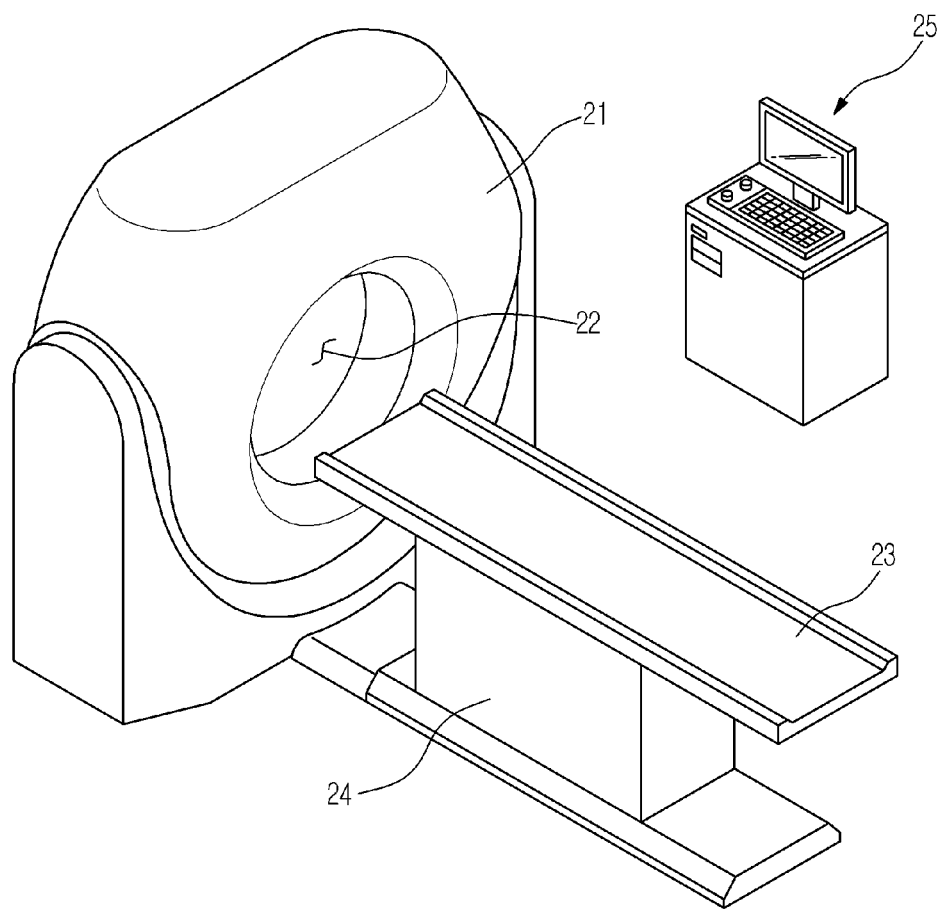
FIG. 13 is a perspective view of a radiographic imaging apparatus according to another exemplary embodiment.
Figure 14A:
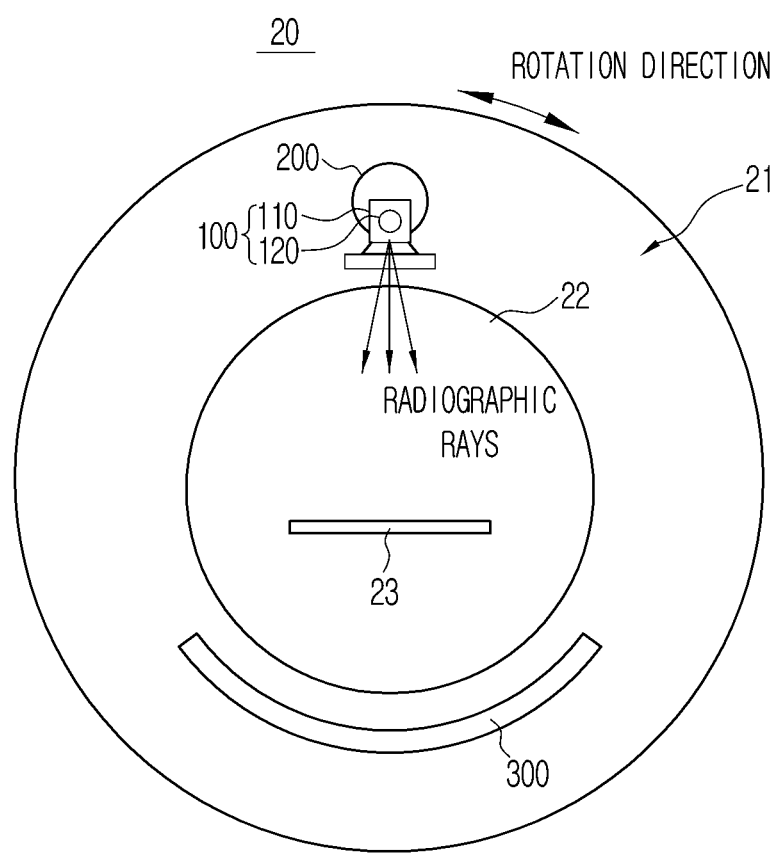
FIGS. 14A and 14B are cross-sectional views of an radiographic imaging apparatus similar to that illustrated in FIG. 13 according to one or more exemplary embodiments.
Figure 14B:
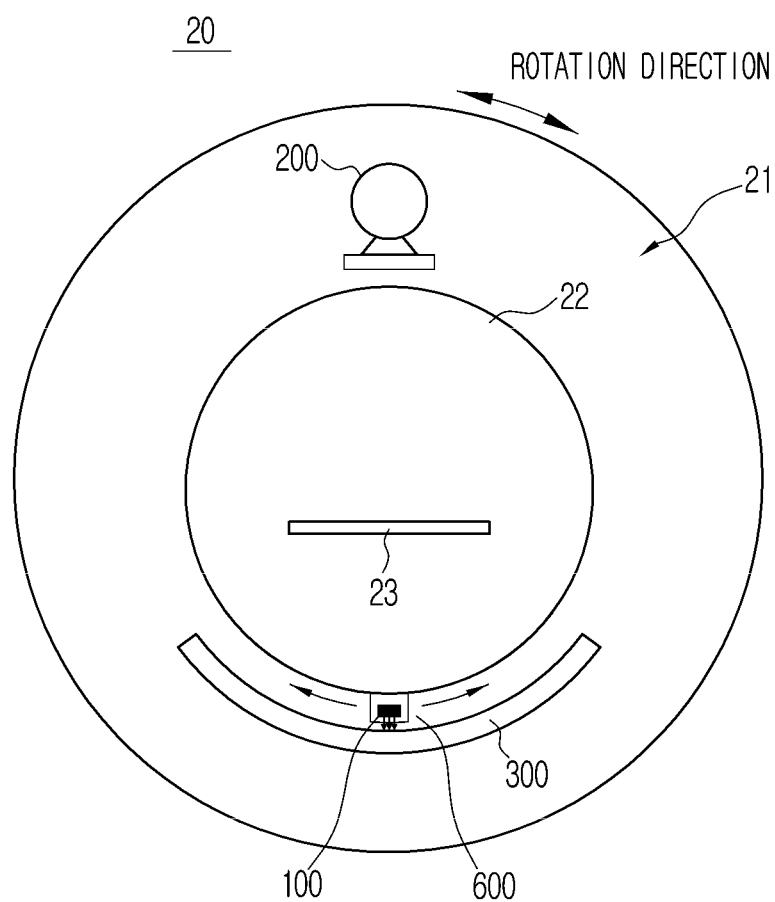

FIG. 13 is a perspective view of a radiographic imaging apparatus 20 according to still another exemplary embodiment. FIGS. 14A and 14B are cross-sectional views of a radiographic imaging apparatus similar to that illustrated in FIG. 13. Referring to FIGS. 13, 14A, and 14B, a radiographic imaging apparatus 20 may be a computed tomography (CT) apparatus.

Referring to FIG. 13, the radiographic imaging apparatus 20 may include a housing 21 having a bore 22 formed in a center thereof, a holder 23 that transfers a held object, and a support 24 that supports the holder 23. The holder 23 having a top end on which the object is held, may be transferred to the bore 22 formed in the housing 21 at a predetermined speed.

Furthermore, the radiographic imaging apparatus 20 may include an information processing unit 25 which displays an image of an object according to an exemplary embodiment and to which various control instructions of the radiographic imaging apparatus 20 are input from a user. A display that displays a radiographic image to the user, and a controller 400 described above may be provided at the information processing unit 25.

Referring to FIGS. 13, 14A, and 14B, a gantry may be installed inside the housing 21. A radiographic source, a radiographic generator, and a radiographic detector may be mounted on the gantry.

In this case, the radiographic source 100 may be placed in the radiographic generator 200, as illustrated in FIG. 14A. In this case, the radiographic source 100 may emit radiographic rays only when threshold energy is corrected, and may not emit radiographic rays when a radiographic image is generated according to the radiographic rays generated by the radiographic generator 200. To this end, the radiographic imaging apparatus 20 may have a structure in which the radiographic source 100 may be moved by a movement unit 600.

The radiographic source 100 may be provided adjacent to the radiographic detector 300, as illustrated in FIG. 14B. Furthermore, the radiographic imaging apparatus 20 may further include the movement unit 600 that moves the radiographic source 100 along the radiographic detector 300.

Also, the radiographic source 100 may have a face shape. In more detail, the radiographic source 100 may be spaced apart from the radiographic detector 300 by a predetermined distance. The face-shaped radiographic source 100 may radiate radiographic rays onto the radiographic detector 300 by moving while being spaced apart from the radiographic detector 300 by the predetermined distance. To this end, the movement unit 600 may be provided in the gantry.

Figure 15:
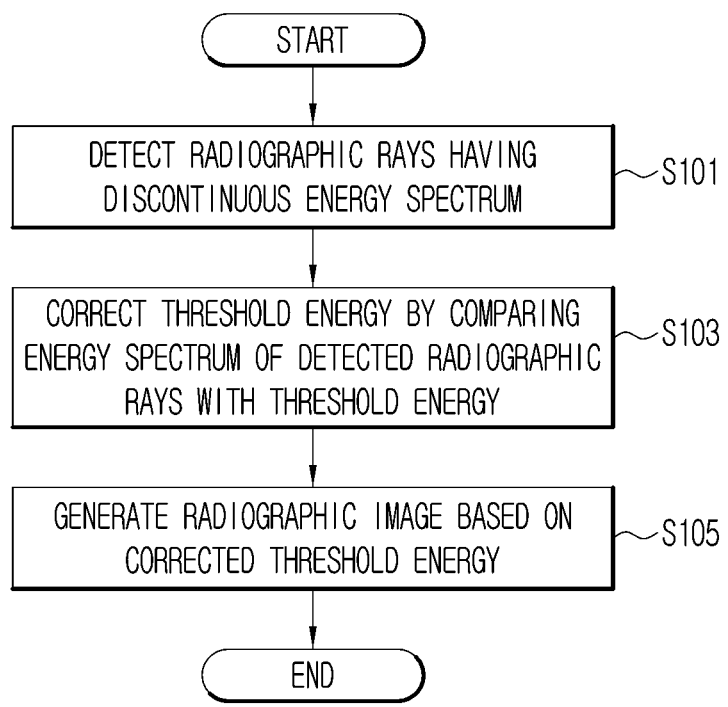
FIG. 15 is a flowchart illustrating a method of controlling a radiographic imaging apparatus, according to an exemplary embodiment.

FIG. 15 is a flowchart illustrating a method of controlling a radiographic imaging apparatus, according to an exemplary embodiment.

Referring to FIG. 15, in Operation S101, the radiographic source 100 radiates radiographic rays having a discontinuous energy spectrum. In more detail, the radiographic source 100 may generate an energy spectrum of the radiographic rays having the discontinuous energy spectrum.

In this case, a photon counting method may be used in radiographic detection. Here, the radiographic rays having the discontinuous energy spectrum may be radiographic rays emitted by a radiographic isotope, such as Am-241, Cd-109, and Co-57.

In more detail, in Operation S101, the energy spectrum of the radiographic rays may be generated by varying threshold energy of pixels in a predetermined unit and by counting and storing the number of photons having energy that exceeds threshold energy.

Alternatively, the energy spectrum of the radiographic rays may be generated according to the pixels by storing only energy, of which the number of photons having energy that exceeds threshold energy varies rapidly (for example, when the number of photons counted compared to previous threshold energy increases or is reduced by 30%) in a format in which only characteristic energy of the energy spectrum is stored.

In Operation S103, the comparator 420 and the correction unit 430 correct threshold energy by comparing the energy spectrum detected in Operation S101 with an eigen energy spectrum of the radiographic rays. Here, the eigen energy spectrum may be an energy spectrum detected in an ideal pixel, and the detected energy spectrum may be an energy spectrum detected in each pixel in Operation S101. This will be described below with reference to FIG. 16 in more detail.

In Operation S105, the image processor 500 generates a radiographic image based on the corrected threshold energy. In more detail, the radiographic rays are radiated onto the object, and the radiographic rays transmitted by the object are received, and the number of photons included in the received radiographic rays is counted according to the corrected threshold energy. Next, a radiographic image is generated based on information regarding the number of photons counted in each pixel.

FIG. 16 is a flowchart illustrating a method of correcting a threshold energy similar to Operation S103 of FIG. 15 according to an exemplary embodiment. Hereinafter, a method of correcting the threshold energy, similar to Operation S103, will be described with reference to FIG. 16 in detail.

Referring to FIG. 16, in Operation S201, the number of photons having energy that exceeds threshold energy may be counted and stored.

Energy in which discontinuity is generated, is detected from an energy spectrum detected in Operation S201. In more detail, the energy in which discontinuity is generated, is detected from the energy spectrum detected in each pixel. In this case, the energy in which discontinuity is generated, is energy, of which the number of photons counted varies rapidly, and a base on which the number of photons varies rapidly, may be set by the user. For example, when the number of photons increases by a predetermined reference percentage or more, or is in a preset range or more, energy having the number of photons descried above may be detected as energy in which discontinuity is generated.

When the energy spectrum is generated by storing only energy that varies rapidly in Operation S101, Operation S201 may be omitted.

In Operation S203, energy of the received radiographic rays in which discontinuity is generated, may be compared with detected energy. To this end, energy of the received radiographic rays in which discontinuity is generated, may be separately stored.

In more detail, in Operation S203, a difference between energy (for example, 22 keV, 25 keV, and 88 keV of FIG. 3A) in which discontinuity is generated from the eigen energy spectrum of the received radiographic rays and energy (for example, 45 keV, 46 keV, and 60 keV of FIG. 10A) in which discontinuity is generated from the detected energy spectrum, may be calculated.

In Operation S205, values of threshold energy to be corrected may be calculated based on a result of comparison calculated in Operation S203. In more detail, threshold energy of the pixels may be linearly corrected based on the result of comparison, or the threshold energy of the pixels may be calculated according to a predetermined function.

The threshold energy to be corrected may also be calculated using a predetermined value according to the difference values of energy. In this case, a database in which the values of threshold energy to be corrected according to the difference values are stored, may be used, and the database may be created through experience rules or experiments.

In Operation S207, a mapping table may be updated according to the corrected threshold energy. Here, information regarding the threshold energy to be applied according to pixels is defined in the mapping table. The mapping table may be, for example, a database configured of a secondary matrix.

In Operation S209, the energy spectrum may be checked again according to the updated mapping table. In more detail, threshold energy of each pixel is set according to the threshold energy value stored in the mapping table, and radiographic rays are uniformly radiated onto each pixel, and it is checked whether the number of photons detected in each pixel is present within a predetermined range, and it is determined whether threshold energy correction is well performed.

As described above, in a radiographic imaging apparatus and a method of controlling the same according to the one or more exemplary embodiments, a more precise and appropriate image regarding an internal structure of an object onto which radiographic rays are radiated, can be obtained.

Furthermore, threshold energy of the radiographic imaging apparatus is adjusted using at least one radiographic isotope having a discontinuous energy spectrum so that a limitation of precision can be overcome and an error caused by non-uniformity of each pixel can be minimized.

Although a few exemplary embodiments have been shown and described, it would be appreciated by those skilled in the art that changes may be made in these exemplary embodiments without departing from the principles and spirit, the scope of which is defined in the claims and their equivalents.

What is claimed is:

1. A radiographic imaging apparatus comprising:
a radiographic source configured to emit radiographic rays in a discontinuous eigen energy spectrum;
a radiographic detector configured to receive the radiographic rays, convert the received radiographic rays into electrical signals, and count the number of photons having energies that exceed a threshold energy; and
a controller configured to adjust the threshold energy by comparing an spectrum of the received radiographic rays with the eigen energy spectrum of the emitted radiographic rays from the radiographic source.

2. The radiographic imaging apparatus of claim 1, wherein the radiographic source comprises at least one radiographic isotope.

3. The radiographic imaging apparatus of claim 2, wherein the at least one radiographic isotope is at least one selected from the group consisting of americium-241, cadmium-109, and cobalt-57.

4. The radiographic imaging apparatus of claim 2, wherein the at least one radiographic isotope is at least one selected from the group consisting of a dot-shaped radiographic source, a line-shaped radiographic source, and a face-shaped radiographic source.

5. The radiographic imaging apparatus of claim 1, wherein the radiographic source further comprises:
a shielding unit configured to shield the radiographic rays.

6. The radiographic imaging apparatus of claim 5, wherein the shielding unit is further configured to guide the radiographic rays along a radiation direction.

7. The radiographic imaging apparatus of claim 1, wherein the controller comprises:
a spectrum generator configured to generate an energy spectrum according to pixels of the radiographic detector by varying the threshold energy;
a comparator configured to compare the discontinuous eigen energy spectrum with the generated energy spectrum; and
a correction unit configured to adjusts the threshold energy based on a result of comparison from the comparator according to the pixels of the radiographic detector.

8. The radiographic imaging apparatus of claim 7, wherein the controller further comprises:
a mapping table in which values of the threshold energy are configured to be stored according to the pixels, and
wherein the correction unit is further configured to update the mapping table according to the adjusted threshold energy.

9. The radiographic imaging apparatus of claim 8, wherein the controller further comprises:
a testing unit configured to set threshold energy of the pixels according to the updated mapping table and determine whether errors of the pixels are within a predetermined range.

10. The radiographic imaging apparatus of claim 1, further comprising:
a movement unit that moves the radiographic source so that the radiographic rays emitted from the radiographic source are uniformly radiated onto the radiographic detector.

11. A method of controlling a radiographic imaging apparatus, wherein the radiographic imaging apparatus receives radiographic rays and counts the number of photons having energies that exceed a threshold energy based on the received radiographic rays, the method comprising:
detecting, using a radiographic detector, an energy spectrum of radiographic rays in a discontinuous energy spectrum; and
adjusting, using a controller, the threshold energy by comparing the detected energy spectrum of the radiographic rays in the discontinuous energy spectrum with an eigen energy spectrum of the radiographic rays.

12. The method of claim 11, wherein detecting the energy spectrum comprises:
varying the threshold energy at predetermined intervals; and
monitoring the number of photons counted in pixels of the radiographic detector.

13. The method of claim 11, wherein the adjusting the threshold energy comprises:
calculating a difference value between the detected energy spectrum of the radiographic rays in the discontinuous energy spectrum with the eigen energy spectrum of the radiographic rays; and
determining threshold energy of the pixels based on the difference value.

14. The method of claim 13, wherein the determining the threshold energy comprises:
determining the threshold energy of the pixels by substituting the difference value for a parameter of a predetermined function.

15. The method of claim 11, wherein the adjusting the threshold energy comprises:
updating a mapping table in which the threshold energy is stored according to the pixels.

16. The method of claim 15, wherein the adjusting the threshold energy further comprises:
checking whether errors of the pixels are within a predetermined range, by setting the threshold energy according to the updated mapping table.

17. The method of claim 11, further comprising:
counting the number of photons included in the radiographic rays transmitted by an object based on the adjusted threshold energy; and
generating a radiographic image based on the counted number of photons.

18. A radiographic imaging apparatus comprising:
a radiation source configured to transmit radiation at a transmission energy level;
a detector configured to receive, at a pixel of the detector, the radiation at a received energy level;
a controller configured to store an energy spectrum of the radiation, wherein the energy spectrum is generated by comparing the transmission energy level and the received energy level and determining a difference, generating a correction value using the difference, adjusting the received energy level using the correction value, and storing the adjusted received energy level into the energy spectrum.

19. The radiographic imaging apparatus of claim 18, wherein the controller is configured to store the adjusted received energy level into the energy spectrum in response to a change in the adjusted received energy level compared to a previous energy level is over a threshold.

20. The radiographic imaging apparatus of claims 18, wherein the radiation source is further configured to transmit radiation at a plurality of transmission energy levels, and wherein the detector is further configured to receive, at a plurality of pixels of the detector, the radiation at a plurality of received energy levels.

\* \* \* \* \*